United States Patent
Canda et al.

(10) Patent No.: US 9,058,545 B2
(45) Date of Patent: Jun. 16, 2015

(54) AUTOMATIC REGISTRATION OF IMAGE PAIRS OF MEDICAL IMAGE DATA SETS

(71) Applicants: Valer Canda, Erlangen (DE); Christian Lange, Eggolsheim (DE)

(72) Inventors: Valer Canda, Erlangen (DE); Christian Lange, Eggolsheim (DE)

(73) Assignee: Siemens Aktiengesellschaft, Munich (DE)

( * ) Notice: Subject to any disclaimer, the term of this patent is extended or adjusted under 35 U.S.C. 154(b) by 224 days.

(21) Appl. No.: 13/751,569

(22) Filed: Jan. 28, 2013

(65) Prior Publication Data

US 2013/0195329 A1 Aug. 1, 2013

(30) Foreign Application Priority Data

Jan. 27, 2012 (DE) .......................... 10 2012 201 169

(51) Int. Cl.
G06K 9/62 (2006.01)
G06T 7/00 (2006.01)
G06F 19/00 (2011.01)

(52) U.S. Cl.
CPC ............ *G06K 9/6267* (2013.01); *G06F 19/321* (2013.01); *G06T 7/0038* (2013.01); *G06T 2207/10072* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 2005/0113961 A1 | 5/2005 | Sabol et al. | |
| 2006/0015494 A1* | 1/2006 | Keating et al. | 707/6 |
| 2008/0118130 A1* | 5/2008 | Pillai et al. | 382/131 |
| 2009/0097778 A1 | 4/2009 | Washburn et al. | |
| 2009/0190840 A1 | 7/2009 | Gundel | |
| 2009/0292559 A1* | 11/2009 | Ranjan et al. | 705/3 |
| 2010/0312100 A1 | 12/2010 | Zarkh et al. | |
| 2012/0099769 A1* | 4/2012 | Eichhorn | 382/128 |
| 2012/0134562 A1 | 5/2012 | Boettger et al. | |

FOREIGN PATENT DOCUMENTS

DE    10 2011 007 341 A1    12/2011

* cited by examiner

*Primary Examiner* — Jon Chang
(74) *Attorney, Agent, or Firm* — Schiff Hardin LLP

(57) ABSTRACT

In a method, device and storage medium encoded with programming instructions for automatic image registration of image data of a current medical image MR study and at least one reference study, corresponding image pairs of the current study and the reference study are formed automatically with an association machine without needing the analyze the respective image data or pixel data. The pair determination takes place exclusively on the basis of the DICOM header data. A synchronized image processing and/or presentation of the generated image pairs takes place at a monitor.

12 Claims, 7 Drawing Sheets

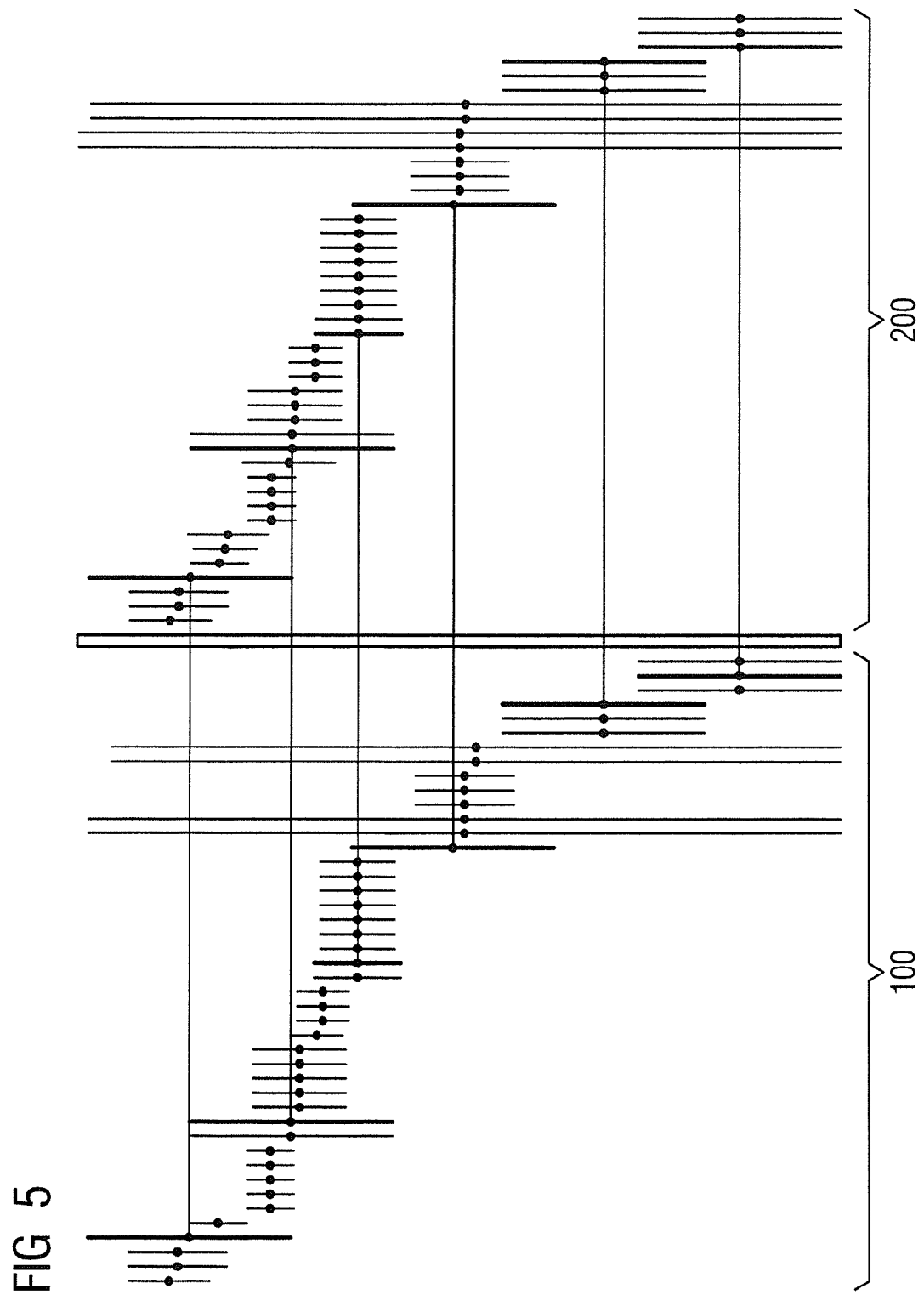

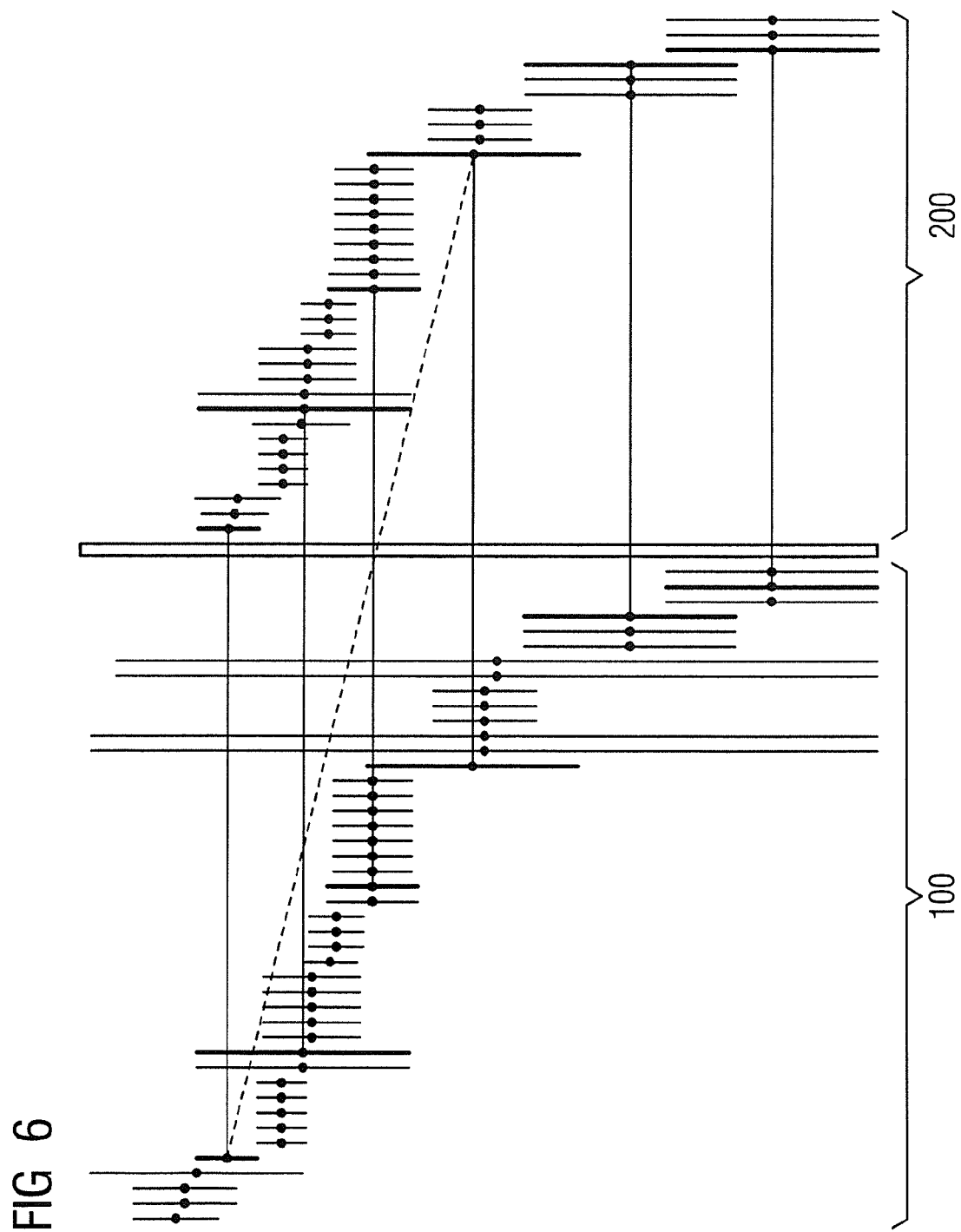

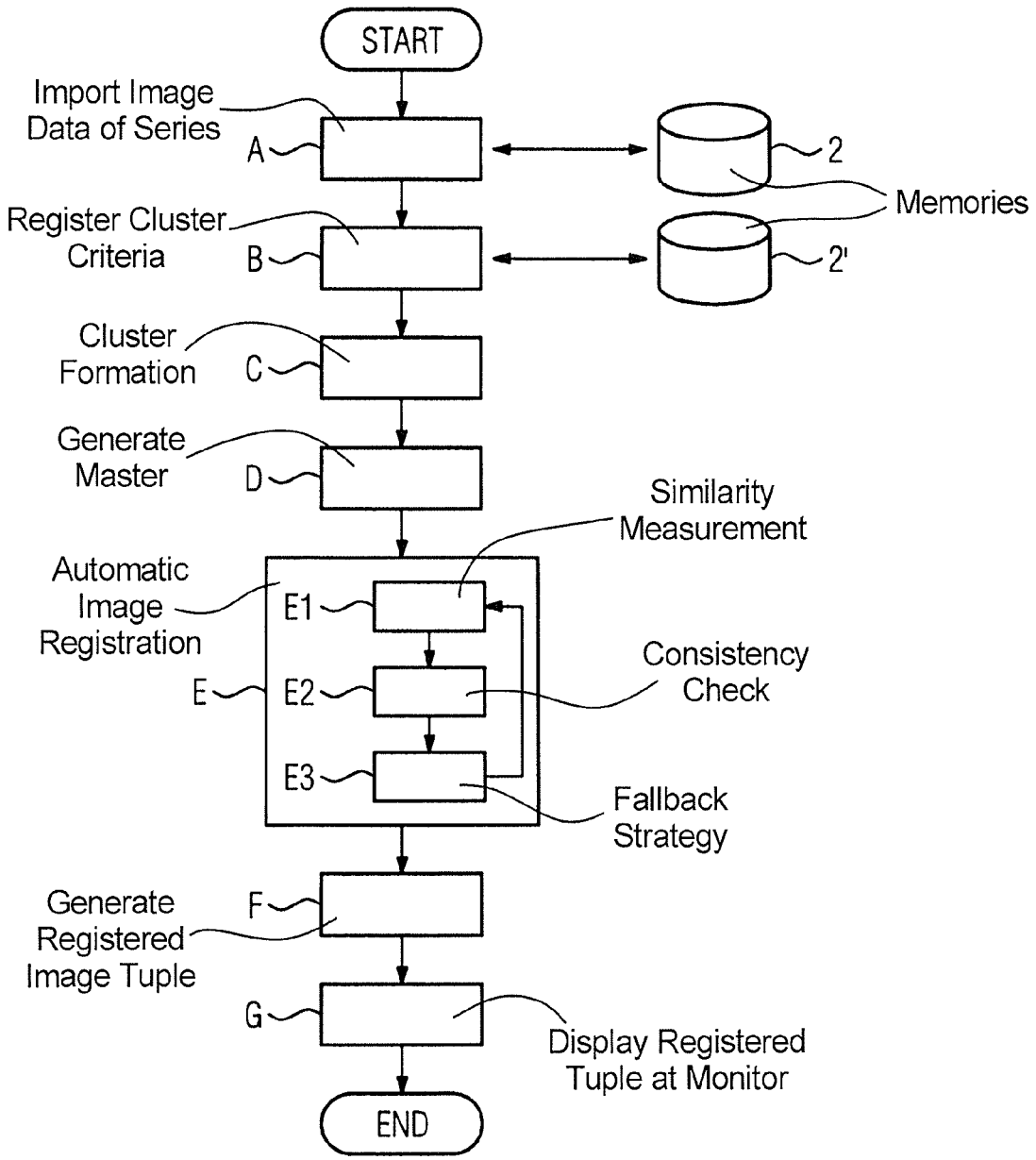

AUTOMATIC REGISTRATION OF IMAGE PAIRS OF MEDICAL IMAGE DATA SETS

BACKGROUND OF THE INVENTION

1. Field of the Invention

The present invention is in the field of medical technology and information technology, and in particular concerns an approach in order to register image data from different image series in order to associate these with one another and to be able to present or process these images on a monitor in synchronization.

2. Description of the Prior Art

In examinations known as multi-region magnetic resonance tomographic examinations, for which measures are executed for different body regions at different points in time, the problem is presented of structuring the multiple acquired image data sets so that they can be presented on a monitor synchronously, and thus so as to be cognitively evaluable by an assessor.

However, in addition to the mere presentation of images, image registration is also required for many different image calculations, processings and evaluations. If, for example, it is desirable to offset a series from the current examination and a series from a previous examination with respect to one another, these series must be registered with each other (brought into registration). The "offsetting" can extend from a simple image subtraction to complex statistical contrast variation calculations or tumor growth calculations. In principle, two-dimensional or three-dimensional acquisitions of the human body or of specific body parts, organs or tissue structures are generated within the scope of the image acquisition (for example with the modalities MRT, CT, PET, etc.). In order to enable an overview of the chronological development of the body structures (for example of tumor tissue) in the acquired image data, these acquisitions are normally repeated at a later point in time. In the assessment of these exposures, the radiologist would typically like to consider the current image data together with specific or selected available images from pre-examinations so that he or she can better assess anatomical or pathological variations.

Many different finding systems (normally software-based) are presently operated with which a finding based on different image data of different series should be executed. For this purpose, current image data sets must be associated and registered with image data sets of prior examinations in order to present these synchronously. The image registration includes a transformation of the spatial coordinates of a first image with those of the second image. Depending on the type of acquisition method or the modality that is used, the image registration is a necessarily complex task. In contrast to CT or PET examinations in which only a few image volumes with respective large spatial coverage are normally created, in MR examinations ("magnetic resonance tomography") a number of smaller image volumes are normally acquired. Depending on the examination, up to 30-40 image volumes can be produced. The problem is then presented that the "correct" image data of the prior examination must be combined with the respective "correct" image data of the current examination.

In the prior art, known software-based solutions for the image registration task described in the preceding are normally based on an automatic image registration, and apply one of the following strategies for image registration.

1. A representative series (image volume) of a current examination is registered with a representative series of the previous examination. The series that best (as extensively as possible) characterizes the properties of all image volumes of the respective study is typically defined as a representative series. An explicit registration is then executed between the representative series of the current examination and the representative series of the previous examination. All remaining registrations between the two series (previous examination and current examination) can then be calculated via implicit identity registrations. However, this approach leads to a limited registration precision in the peripheral body regions. Therefore, this approach is not applicable to multi-region MR examinations, or can only be applied with quality losses.

2. All possible combinations of image data sets are combined. In this approach all series pairs are registered with one another for which a synchronized presentation or processing could potentially be required. This approach is based on the "Small World Phenomenon" and is extremely computationally intensive, and therefore time-consuming. Moreover, the approach has the disadvantage that it is not applicable in multi-region MR examinations since here multiple body regions of the patient are scanned, and thus image data sets of multiple studies (that for their part comprise multiple series) are acquired, which overall makes the combination job still more complex in its design.

An additional disadvantage of the first approach is that a representative series with sufficient spatial coverage must be determined for both the current examination and for the previous examination. In contrast to computed tomography, no such representative series (that, moreover, has a sufficient registration precision) is normally found in multi-region magnetic resonance tomography. This is based on the physical fact that, given an MR examination with sufficient spatial coverage, the examination is normally executed over a long period of time, which in turn limits the registration precision because it is very likely that the patient will move somewhat during a long examination duration.

SUMMARY OF THE INVENTION

In view of the disadvantages of the known finding systems, an object of the present invention is to automate and improve the registration between different image data sets of an MR study and a reference study (for example a previous examination). In particular, the automatic registration for multi-region MR studies should be improved. Furthermore, the automatic registration procedure should be improved with regard to registration precision and performance parameters. Moreover, resources of the computer or of the computer platform should be better used and conserved with regard to the image registration job.

In the following, the invention is described based on the inventive method. Advantages, features and alternative embodiments are also applicable to the other achievements of the object, namely an apparatus and a non-transitory, computer-readable data storage medium. The features of the method are implemented by device-related features (in particular microprocessor modules) that are designed with the corresponding functionality of the respective method features. The same also applies in reverse, such that described features of the device can also be used as a development of the method since (for informatics) whether implemented in software or hardware makes no difference for the achievement of the object according to the invention.

According to one aspect, the present invention concerns a computer-implemented method for automatic registration of image data that originate from magnetic resonance tomography measurements, and in particular of image data of an MR study and image data of at least one reference study for the purpose of a synchronized presentation of image pairs or image tuples (wherein an image pair is respectively formed from image data of a first MR study and associated or corresponding image data of a second reference study) on a monitor, wherein the studies each include multiple series of slice images. The method according to the invention the following method steps:

The following method step is executed at least for the MR study:
automatic generation of clusters of image data of all series of cluster criteria that are based exclusively on DICOM header attributes.
The following is executed for all clusters:
determine a respective master (for a cluster).
Automatic registration of the image data of the MR study with the image data of the reference study to form registered image pairs (or image tuples, given multiple reference studies), in which similarity measurement is implemented for each respective master from the MR study to search for at least one reference study that satisfies preconfigurable similarity conditions, or to search for a similar reference master of the reference study.

The terms used herein are defined in detail in the following.

The method is computer-implemented and runs wholly automatically, i.e. without any manual interaction by a user. The method can be partially or entirely software-based. Moreover, it is possible to embed or integrate the method or system as an embedded system in the MRT system and/or in an image processor (for example within the scope of the post-processing). The method serves to store, process and relay prepared data (in the form of image tuples or associated image units) using computer-based technical devices (network) at other instances. According to the invention, the input variables for calculation and/or processing (the set of individual slice images) are addressed differently (as tuples, in synchronized form), and thus are stored in a modified form. The method therefore also takes into account the conditions of the data processing system in that an associated, synchronized pair formation for faster presentation and image processing is enabled for additional calculation steps.

The method serves for registration of image data that originate from different MR studies. The method generates registered image pairs or registered image tuples (in the event that the MR study should be compared with multiple reference studies) from a set of individual images in a fully-automated process. The generated image pairs or image tuples can then be presented in a synchronized manner on at least one monitor (multiple monitors can by all means also be used) or another presentation device (projector, printer etc.). This presentation facilitates the situation that often occurs in the context of a medical diagnosis, that, within the scope of making a finding, a physician must frequently compare current image data sets of an MR study with image data sets of a prior study (reference study), for example in order to be able to assess a tumor growth. For this it is necessary that the respective corresponding slice image exposures are associated with one another correctly and thus (associated, and therefore synchronized) can be presented. This is achieved with the proposal according to the invention.

As used herein, the "registration" of image data relates not only to the use of the term in the sense of a spatial transformation between two images or image volumes (as is typical in image processing), but also relates to the generation of image pairs or image tuples for synchronized processing and/or presentation. The term is thus to be understood in the sense of a registration pair determination and subsequent image registration. An important feature of the Application is a specific, automatic and performant pair determination. The registration is thus an automatic association or, respectively, mapping process. The registration can be executed using multiple stores for intermediate storage of the data.

The term "image data" relates to image data that are acquired within the scope of a magnetic resonance tomography measurement or examination (data acquisition). These can be two-dimensional or three-dimensional image data sets. In a preferred embodiment, the invention concerns image data that have been acquired with a multi-region MR examination. A multi-region examination is characterized in that multiple or all body regions of a patient are scanned (from head to foot, so to speak). 30-40 smaller image volumes are normally acquired.

A (current) MR study is typically compared with a reference study (a prior examination/prior study). However, it is alternatively also possible to compare a current MR study with multiple prior examinations or reference studies. In this case, registered image tuples are generated. The MR study and the reference study(s) differ in their acquisition point in time. They thus concern different health states (points in time) of the patient.

In a preferred embodiment of the invention, the protocol for the image data sets is based on a DICOM standard (DICOM: Digital Imaging and Communications in Medicine). The invention is thereby not based on a specific version of the DICOM protocol. Alternatively, a different standard for data exchange of medical image data can also be used. According to the DICOM standard, a DICOM object has a DICOM header and DICOM image data. The DICOM header has multiple properties (attributes) and additional parameters that relate to the respective pixel data, for example the attribute "Body Part Examined", the size of the pixel data, the acquisition point in time of the pixel data, the spatial coordinates of the pixel data etc. It is possible to separately access the (low-volume) header data and the (high-volume) pixel data. In other words, it is possible to read out header data without needing to explicitly access pixel data. Since the header data are significantly less comprehensive, the access to the header data can be executed quickly and efficiently. The image data are the actual pixel data (the presentation of the respective organ or body region).

According to the DICOM standard, an MR study includes at least one series (normally multiple series). For example, a series can relate to a defined body region (for example neck, thorax, abdomen etc.). A series, in turn, includes a number of slice images. It follows that a comprehensive, complex set of slice images is generated in the event that multiple body regions of a patient are acquired in multiple studies. An automatic association of the acquired image data with anatomical body regions and/or with other image data is therefore of particular importance.

The term "clusters" concerns the automatic generation of clusters. This takes place wholly automatically according to preconfigurable cluster criteria. A cluster is a group formation according to defined properties. The clusters thus comprise image data or, respectively, slice images that have specific cluster criteria in common. According to a significant aspect of the invention, the cluster criteria are based exclusively on DICOM header attributes. The cluster criteria can thus be read out very quickly from the DICOM header. The cluster criteria are advantageously based on the spatial coordinates of the examined body region. Alternatively (and in the event that it reliably exists), the header attribute "Body Part Examined" can also be resorted to (however, this attribute is not absolutely necessary for the realization of the achievement of the object according to the invention, such that at this point it is expressly indicated that an image registration/image pair registration is also executed without the header attribute "Body Part Examined").

The term "Master" characterizes a representative of a cluster. It is thus a cluster master. The master is advantageously determined for a cluster in that it satisfies preconfigurable master criteria. The master criteria are typically the parameters of spatial coverage and resolution. In other words, that image data set from the cluster that has the greatest spatial coverage within the cluster and a maximum resolution is advantageously determined as a master. In other embodiments, other master criteria can be defined and/or preconfigured here so that the spatial coverage and the resolution are not the sole criteria for the master determination. Additional criteria are, for example, a number of slices (in order to penalize localizers), an image type (in order to penalize composite images or TimCT images, and thus to prefer the local, body region-specific registrations), which can be used as a fine tuning.

The process of the registration of the image data relates to an automatic association of image data sets of the MR study with image data sets of at least one reference study. Registered image pairs or image tuples are thus generated. The registration can therefore also be understood as fully automatic, bijective association of image data of the MR study with image data of the at least one reference study.

According to a preferred embodiment, two variants are provided for the automatic registration of the image data.

1. In this first variant, not only are image data of the current MR study clustered, the reference study(s) to be compared are also clustered. After application of this step, both clusters of the current MR study and clusters of the reference stud(y/ies) are present. A master is determined for all clusters. The master of the current MR study can accordingly be compared with the masters of the reference stud(y/ies) according to preconfigurable similarity conditions. In particular, a master of a current MR study is associated with the master of the at least one reference study that it most closely resembles.

2. In these two embodiment variants, only the current MR study is clustered. The reference studies are not clustered. For each master of the MR study (the method is iteratively applied to all masters of the MR studies), the respective most similar series of the reference study is determined. preconfigurable similarity conditions are thereby accessed. The similarity measurement is advantageously based on the measurement of the similarity with regard to the series name. In particular the DICOM header attribute "Series Description" can be used here. In advantageous developments of the invention, the measurement of similarity can take into account additional DICOM attributes, for example image properties (for example greyscale histograms etc.).

In an embodiment, the method includes the additional method step of the synchronized presentation and/or the synchronized processing of the registered data sets. This allows display on a monitor, in a synchronized manner of the generated registered image pairs or image tuples of the MR studies that are to be compared. The current study is thereby presented simultaneously on the monitor with the reference studies to be compared. Different windows for the study and the reference studies are typically provided in which the respective corresponding images are displayed, and thus can be compared at a glance. A significant advantage of this embodiment according to the invention is that no user interaction whatsoever is necessary in order to prepare the image data for finding and for synchronized presentation. In particular, it is not necessary to access the image content (i.e. pixel data) and to analyze these in order to be able to execute the image registration. According to a further embodiment of the invention, it is provided that the registration method comprises a consistency check. Within the scope of the consistency check, an average displacement vector is calculated for all or for selected, registered image pairs (or, respectively, image tuples), and those registered image pairs that deviate from the average displacement vector beyond a preconfigurable tolerance measure are detected as inconsistent and/or separated out (advantageously automatically). The displacement vector is calculated automatically via subtraction of middle point coordinates of the reference series of the reference study from the middle point coordinates of the current MR series of the MR study. A selected image pair is typically determined for the middle point coordinate subtraction. This can be an average image pair made up of MR study and reference study. Moreover, it is possible to use the master here. Since it can be assumed from this that the anatomical conditions of a patient are approximately stable, the position-related data or, respectively, the spatial coordinates between the image pairs must also approximately coincide. In other words: it can be assumed that the individual displacement vectors of the registered image pairs must be approximately parallel. In the event that an image pair is identified that has a significantly different orientation (in particular a markedly differently directed displacement vectors) in comparison to the other image pairs, this image pair is assessed as suspect. Depending on the degree of deviation from a statistical mean value for the displacement vector, and depending on a preconfigurable tolerance threshold (tolerance measure), this image pair can be separated out as incorrect. Depending on the embodiment, the displacement vector can be calculated for all registered image pairs or only for selected image pairs and be used for a consistency check. The significant advantage is apparent in that inconsistent registration pairs can be sorted out automatically, for example in the event that two studies with markedly different measurement programs must be used as an input value for the image registration.

According to a further embodiment of the invention, after sorting out a registered image pair, a fallback strategy can automatically be used. The fallback strategy is based on the fact that a respective next-best candidate for a master of the reference stud(y/ies) that best satisfies the preconfigured similarity conditions is sought with regard to the respective master of the MR study. With this embodiment the robustness of the automatic image registration can advantageously also be increased in difficult cases. The fallback strategy is also advantageously based on the fact that an image registration is possible without knowledge of image content and without access to the pixel data. The fallback strategy is executed exclusively based on the DICOM header data. In the event that a potentially registered image pair has thus proven to be inconsistent relative to the other image pairs (in particular because the displacement vector is not parallel to the statistical mean of the displacement vectors), the measure of similarity is executed with the additional candidates of the reference slice images in order to find the next best candidates that satisfies the similarity conditions. Because the next best candidate has been found, the consistency check can in turn be executed in order to compare the displacement vector with the average displacement vector. Given agreement, the image pair that is determined in such a manner is registered. Otherwise (thus given an absence of parallelism of the respective displacement vectors), the measure of similarity is implemented for the next candidates of the reference slice images. This method can thus be executed until a suitable candidate for a corresponding slice image can be found for the respective master of the MR study. Depending on the selection of the embodiment variant, it is possible to also cluster the reference study. In this case, the reference study is clustered according to the same cluster criteria as the MR study. The subsequent measure of similarity can then be executed between the respective masters of the MR study and the respective masters of the clustered reference study. However, the clustering of the reference study is not absolutely necessary and can also be omitted in alternative embodiments. In this case, the master of the current MR study is compared for similarity with the individual series of the reference study.

As was mentioned above, the cluster criteria are based on at least one DICOM header attribute which can be accessed independent of the pixel data (thus of the actual image content). The DICOM header attribute or attributes that is/are used for the cluster criteria is/are based on position information of the examined body regions (normally spatial coordinates).

The measure of similarity can be a parsing, a processing and/or an analysis of the DICOM header data. In particular, a name attribute that can identify the respective examined body region (for example an anatomical region such as neck, chest, abdomen etc.) or other characteristic series properties (such as the MR acquisition technique, image orientation, contrast agent administration etc.) of the respective image data is compared for similarity or, respectively, agreement.

A significant feature of the present invention is that the entire method is executed wholly automatically and without user interaction. In particular, the clusters, the determination of a master and/or the registration are executed wholly automatically, in particular using position data and without access to the content of the respective image data (pixel data).

According to a further embodiment of the invention, an automatic optimization is provided in which each image series of the cluster is examined for coordinate agreement with the master. The optimization strategy is executed after the clustering and the master determination.

The optimization step ensures that each series was associated precisely with the cluster whose master it is most closely situated to. For this purpose, additional, fully automatically implemented check steps can optionally be implemented after the initial clustering. Here the position data for each series in the cluster are compared with the position data of their own master and the masters in the neighboring clusters. If the master of a neighboring cluster should be closer to the series than the master of its own cluster (this can occur in particular for a series at the edge of the cluster), the series is shifted into the other cluster.

The above object also is achieved in accordance with the invention by a computerized device for automatic image registration of an MR study and at least one reference study for the purposes of synchronized presentation of the respective image data. The device has an import interface via which image data of the studies are imported. The input interface can be engaged in a data exchange with a memory.

The device additionally has a cluster module. The cluster module is designed to import image data of all series of at least the MR study (optionally also for the reference study) from the memory, and to automatically cluster them according to cluster criteria. The cluster criteria are thereby based exclusively on DICOM header attributes. In other words, the cluster module exclusively accesses the DICOM header in order to apply or execute the cluster criteria. The cluster module can store (buffer) the generated result (the generated cluster) in the data memory.

The device also has a master generation unit. For all clusters, the master generation unit is designed to determine a master for each cluster. The master can also be stored in a separate data memory.

The device also has a registration unit (likewise to be understood in the sense of "pair determination unit") that is designed to automatically register the image data of the MR study with the image data of the reference stud(y/ies). For this purpose, registered image pairs or image tuples are generated in which a similarity measurement is implemented by means of a similarity measurement device for each respective master from the MR study to search for at least one reference study that satisfies preconfigurable similarity conditions, or to search for a similar reference master of the reference study.

The device also has one (or more) monitor(s) (or other output devices) to present the registered image tuples or image pairs.

Moreover, a few additional data memories can also be provided to store the intermediate results or final results of the image registration.

The individual modules and/or units of the device are engaged in a data exchange via a network or via a bus system.

The above object also is achieved in accordance with the present invention by a non-transitory, computer-readable data storage medium encoded with programming instructions that, when loaded into a computerized device as described above, cause the computerized device to implement any or all of the embodiments of the method according to the invention, also described above. The programming instructions can be stored on a portable data medium. It is likewise possible to import the programming instructions from a server via a network and an interface, and to execute the programming instructions at a client. The programming instructions can be provided in the form of a CD, for example.

A number of advantages can be achieved with the invention. A higher precision and a better performance can thus be achieved via the automated image registration. An important advantage is also apparent in that the automatic image registration can be executed without access to the pixel data or without analysis of the image content. The method is therefore very fast. Furthermore, it can be completely automated and can be implemented without user interaction within the scope of the pre-processing. The cluster formation corresponds to a typical body region division that is intuitively selected by the user. However, no image content information is analyzed for the cluster formation. The cluster formation is executed exclusively based on the metadata or, respectively, the header data. Errors that have previously been caused in the prior art due to an incorrect association of image data of a study with reference studies can be avoided with the proposal according to the invention. Overall, the finding quality can be markedly increased.

BRIEF DESCRIPTION OF THE DRAWINGS

FIG. 5 is a schematic image registration of masters according to a preferred embodiment of the invention.

FIG. 6 is a schematic presentation of a consistency check and a fallback strategy within the scope of the automatic image registration according to a preferred embodiment of the invention.

FIG. 7 is an overview presentation of a flow chart according to a preferred embodiment of the registration process of the invention.

DESCRIPTION OF THE PREFERRED EMBODIMENTS

Figure 1:
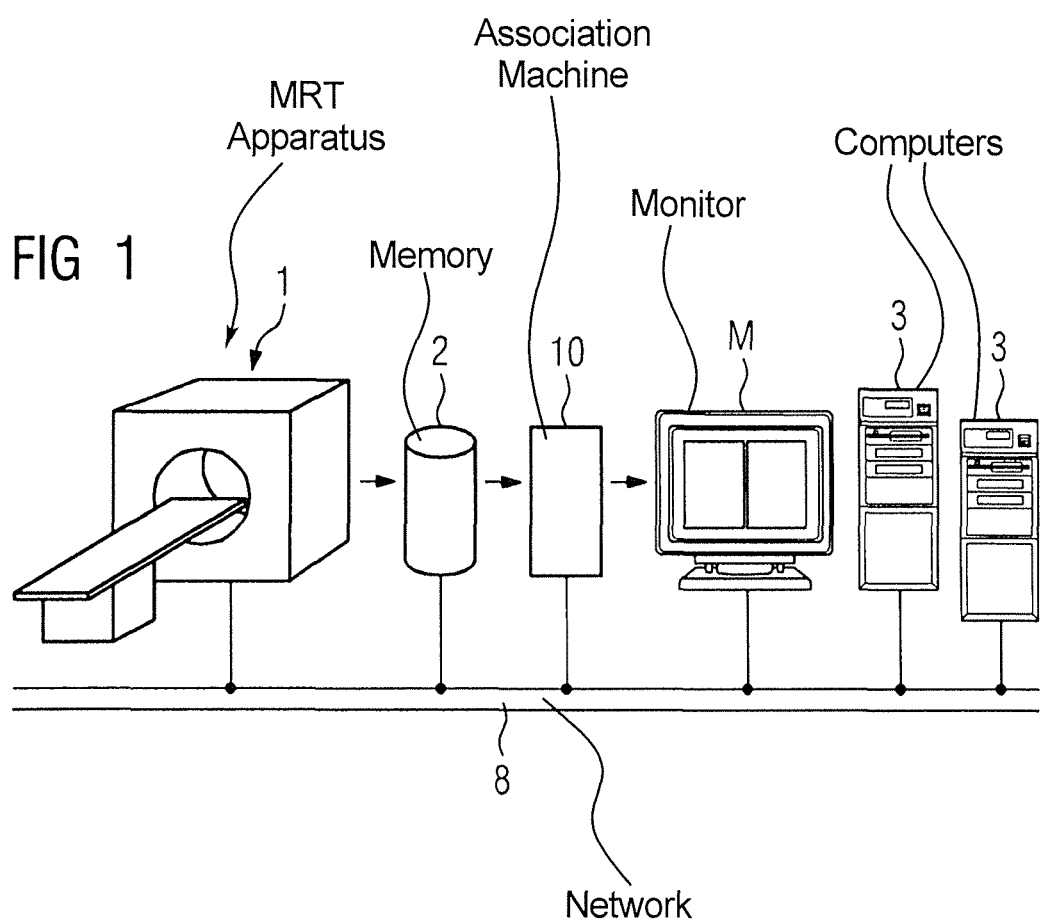
FIG. 1 is a schematic presentation of the context of the automatic image registration.

In the following, the environment of the automatic image registration is explained in detail with reference to FIG. 1. The invention concerns a method and a system for automatic registration of image data that are or, respectively, have been acquired with a magnetic resonance tomography 1 (MRT) apparatus. The acquired image data are stored in a data memory 2. A plurality of data memories are typically provided here for the storage of the acquired image data, since these are very extensive data sets. The data are typically exchanged according to the DICOM standard and are stored in a defined hierarchic data structure that comprises the following hierarchy levels: patient, study, series, image data sets. In particular, multiple studies are normally present with regard to a patient. Each study in turn is composed of a number of series. Each series in turn is composed of a number of slice images or image data sets.

The image data of a current MR study should be associated with image data of previous studies (designated as reference studies in the following). According to the invention, this is executed via an association machine 10. The association machine 10 generates registered image tuples or image pairs and can be designed as part of a computer 3 or a computer system composed of multiple computers (for example a cloud system or a computer network in the sense of a client/server system). The registered image data are subsequently presented synchronously on a monitor M. Image data of the current MR study are presented synchronously in parallel with the respective corresponding image data of the reference studies. All computer-based instances exchange data over a network 8.

Figure 2:
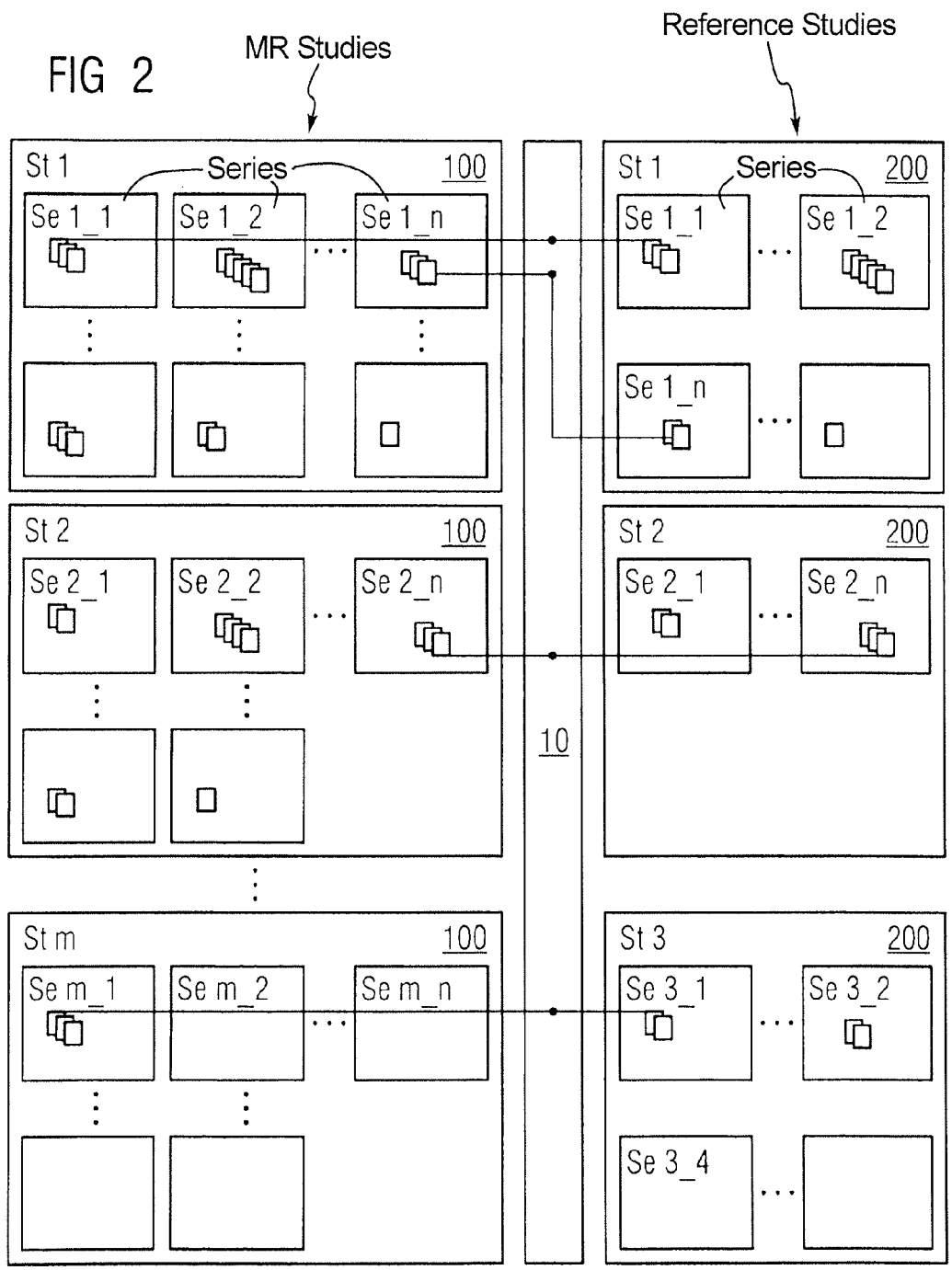
FIG. 2 is a schematic presentation of associations of an association machine according to an embodiment of the invention.

The structuring of the image data is explained in detail in FIG. 2. At least one study is registered in an examination of a patient who is examined by means of a magnetic resonance tomography system 1. A study typically includes multiple series. In FIG. 2, a first study is labeled with the reference character St 1, a second is labeled with St 2 etc., while one series is labeled with Se and a first series is correspondingly indicated with Se 1_1, Se 1_2 (thus with regard to the first two series of the first study). In exceptional cases, a study can also consist of only one series. Particularly in examinations that cover multiple body regions of the patient (known as multi-region examinations), a study St has multiple series Se. Each series Se in turn includes multiple slice image data sets for presentation of the respective examined volume. This is shown in FIG. 2. The studies with the series and the respective slice images for the current MR study that are labeled with the reference character 100 in FIGS. 2, 4, 5 and 6 are located on the left side of FIG. 2. The slice images of the series of the reference studies that have been acquired in the previous examinations and that are labeled with the reference characters 200 in FIGS. 2, 4, 5 and 6 are located on the right side of FIG. 2. Now the respective corresponding image data of the current MR study (shown on the left) should be presented with the respective images of the previous examinations (shown on the right) on a monitor M for the purposes of the finding. The association of the respective corresponding images is executed via the association machine 10. The association machine 10 can be executed wholly automatically so that no user interactions whatsoever are necessary. As shown in FIG. 2, the association machine 10 connects series image data sets of the MR study (so to speak) with corresponding series image data sets of the reference study or the reference studies. The pairing is implemented serially. This is represented in FIG. 2 by the horizontal connecting lines and the connecting points (represented by circles). In this context, "corresponding" means that the first series of the first current study ("head") is associated and registered with the coinciding first series of the second reference study ("head"). If the two series are registered, the first slice image of the one series can be displayed in parallel with the third slice image of the reference series (that anatomically corresponds in one example).

A preferred workflow of a registration method according to the invention is explained in detail in the following with reference to FIG. 7.

After the start of the system in Step A, the image data of the studies to be compared are imported. In particular, access to the data memory 2 is executed for this purpose.

Cluster criteria are registered in Step B. According to a preferred embodiment, position coordinates are read out and evaluated for this. The position-related data can be stored in a data memory 2' in order to read out data of the respective image data sets.

A cluster formation according to the registered cluster criteria takes place in Step C. The image coordinate attributes are typically analyzed for the cluster criterion and supplied to a parsing process. The series are thus clustered into groups in Step C. Depending on the embodiment, it can be provided that different studies are clustered. In a first variant, only the current MR study is clustered (and not the reference studies). In a second variant, in addition to the current MR study all reference studies are also clustered. The generation of multiple series clusters can be provided as a result of the Step C.

A master for a respective cluster is determined in Step D. The master serves as a representative of the respective cluster.

The automatic image registration (as a registration pair determination) follows in Step E. This is executed in multiple sub-steps. A similarity measurement takes place in Step E1 by means of a similarity measurement device 18. This is absolutely necessary in order to find corresponding image data sets between the current MR study 100 and the reference study 200. Steps E2 and E3 are optional, but one or both are provided in a preferred embodiment. A consistency check of the generated image pairs or image tuples takes place in Step E2, and the application of a fallback strategy takes place in Step E3 in the event that an image pair has been detected as inconsistent and a new association is required.

According to the embodiment of these steps, an automatic image registration can be calculated as a result of Step E. For this a registered image tuple is generated in Step F in the event that a current MR study should be compared with multiple previous examination studies. Alternatively, an image pair can be generated in the event that the current MR study should only be compared with one previous study.

The registered image pairs or image tuples can thereupon be synchronously presented at the monitor M in Step G, after which the method ends.

Figure 4:
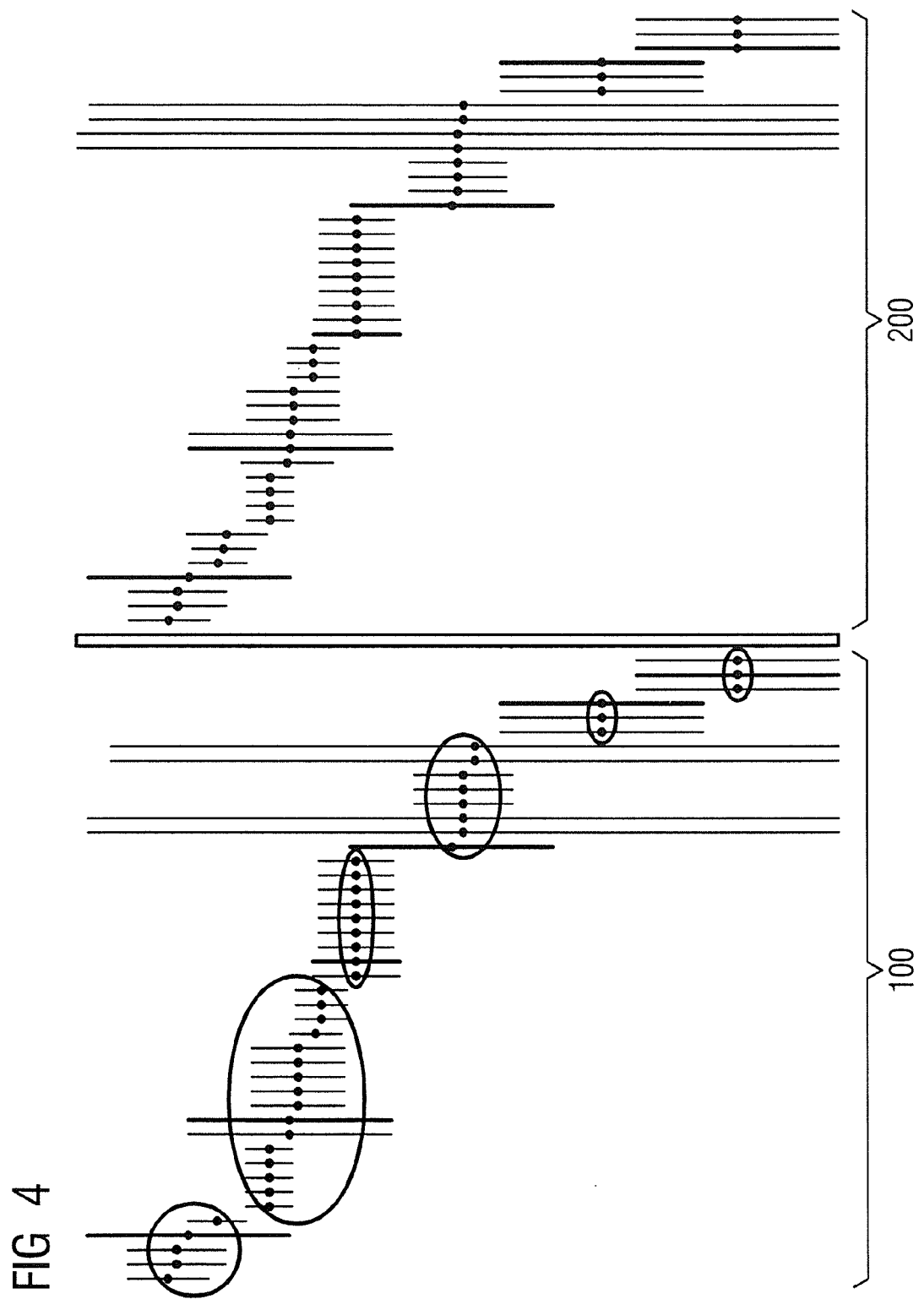
FIG. 4 is a schematic presentation of a clustered MR study in comparison with a reference study.

The cluster formation is explained in detail in the following with reference to FIG. 4. In FIG. 4 the currently clustered MR study 100 is shown on the left side while a reference study 200 is shown on the right side. The vertical lines represent image volumes of a series, wherein the length of the line represents the respective area coverage in the Z-direction (relative to the middle longitudinal axis of the body of the patient or "in the head-to-foot direction"). The area coverage corresponds to the "field of view". The size of the respectively examined organ or body region can be indirectly derived from this. The longer the line in FIG. 4 (and accordingly also in FIGS. 5 and 6), the greater the area coverage or the larger the examined body region. The lines shown in FIGS. 4, 5 and 6 encompass a middle point that is emphasized at points, which middle point is to be used as coordinates for the examined body volume. The current MR study 100, for which 6 clusters have been created, is shown on the left side in FIG. 4. The clusters are respectively represented with ovals around the respective middle points. The first cluster relates to the body regions for "head and neck"; the second cluster relates to the body region "chest"; the third cluster relates to the body region "abdomen"; the fourth cluster relates to "pelvis and composite whole-body images"; the fifth cluster relates to the body region "thigh"; and the sixth and last cluster relates to the body region "lower leg".

A volume is marked as a master for each cluster in FIG. 4. The master is shown in FIGS. 4, 5 and 6 as a thicker line.

After the clustering, an optimization step can optionally be executed in order to ensure that all of those image data that are arranged in spatial proximity to the respective master of the cluster are also located within a cluster. After the cluster formation and the determination of the master for the respective cluster, the association machine 10 can define image pairs for which a registration should occur. This is shown in detail in FIG. 5. For this, in one embodiment of the invention the respective reference study 200 can also be clustered. A master for the respective cluster is then also determined for the reference study 200. The clustering or the cluster criteria coincide for the current study 100 and the prior study 200 in order to be able to generate a measure of comparison. A master of the current study 100 can thereupon be compared very simply with the respective masters of the previous examination 200 (shown on the right) for coincidence or, respectively, similarity. Coinciding masters are represented with a horizontal connecting line in FIG. 5. The masters of the current MR study that is shown on the left side of FIG. 5 are thus registered with the respective corresponding masters of the previous study (shown on the right). Due the anatomical conditions, the respective displacement vectors run approximately parallel between the current MR study and the reference study. This is represented in FIGS. 5 and 6 by the horizontally running, approximately parallel connecting lines.

As an alternative to the embodiment described above, it is also possible to not cluster the reference study 200. In this embodiment variant, a most similar series of the reference study 200 (shown to the right in FIGS. 5 and 6) is sought for each master of the current study 100 (shown to the left). The measure of similarity is based on preconfigurable similarity conditions. According to a preferred embodiment, in particular the similarity of the series name is placed as a similarity condition. This embodiment is fundamentally preferred since it is not necessary here that the current study 100 examines the same body regions as the reference studies 200, and this poses the same requirements for the studies. In this case, an automatic image registration can be executed even when the current MR study 100 has a different cluster count than the reference study 200. This embodiment is thus more robust and can be used more reliably and flexibly than the variant in which the reference study 200 is also clustered. In addition to the series names, additional DICOM attributes can additionally be used that are in particular read out from the header for evaluation of similarity. Moreover, it is also possible to take into account additional parameters (for example statistical information, for example greyscale histogram).

After the association machine 10 has delivered a proposal or, respectively, a design for the image registration pairs, a consistency check and a fallback strategy can optionally be applied. This is explained in detail in the following with reference to FIG. 6. FIG. 6 again shows the current MR study 100 on the left side, which current MR study 100 should be compared with image data sets of a previous examination 200 (shown on the right side in FIG. 6). FIG. 6 shows an example for which the previous examination shown on the right side does not include a body region ("head", in this case). The association machine 10 has clustered the current study 100 in Steps C and D and formed potential registration pairs according to the similarity conditions. The master series of the current head-neck cluster was thereby initially (and incorrectly) paired with the pelvis master of the previous examination 200. This is represented in FIG. 6 with the dashed line running at an angle. The automatic consistency check has detected that the displacement vector of this registration pair does not run approximately parallel to the other displacement vectors (at an angle in FIG. 6). This registration pair is thereupon sorted out. Therefore, in FIG. 6 it is shown only with a dashed line. A fallback strategy that is aimed at finding a correct (better) registration pair for the respective cluster can thereupon be optionally applied. For this, a similarity measurement is implemented for each series of the current cluster in order to find similar reference series. This method can be executed iteratively for all series of the current cluster. In this case, the neck series of the previous examination 200 was found as a corresponding image data set for the registration pair after application of the consistency check and the fallback strategy.

It should be emphasized that the clustering, the master calculation, the pair formation (including the consistency check and the fallback strategy) are based exclusively on header data and are executed without knowledge of the image and without analysis of the pixel data.

As noted above, it is possible in principle to not only compare a current MR examination 100 with a reference study 200 (as is schematically indicated in FIGS. 4 through 6) but to register said current MR examination 100 with multiple reference studies 200. The method described in the preceding would then need to be iteratively applied for the respective studies.

FIG. 3 again shows somewhat more detailed, individual modules of the association machine 10. The association machine 10 is engaged in data exchange with the magnetic resonance tomography system 1. The magnetic resonance tomography system 1 generates a set of individual image data that are labeled with the reference character E in FIG. 3. The individual image data are supplied to the association machine 10. The set of individual images can optionally also be cached in the data memory 2 and/or be imported from this.

The association machine 10 has a cluster module 12 that is designed to group or, respectively, cluster the series with the respective image data. The generation of the cluster takes place without access to the pixel data.

The association machine 10 furthermore has a master generation unit 14 that is designed to determine a master for each of the generated clusters. The determination of the master in particular takes place according to the parameters "maximum area coverage" and "maximum resolution" and is applied to the image data sets within the cluster. Alternatively, the master generation unit 14 operates with additional criteria for master determination (for example number of slices, image type).

Furthermore, the association machine 10 has 1 registration unit (also to be understood as a "registration pair determination unit") 16 that is designed to automatically register the image data. The image pairs or image tuples are formed here. A similarity measurement is thereby executed. A consistency check and a fallback strategy can optionally be additionally applied.

Furthermore, the association machine 10 has a similarity measurement device 18 that is designed to execute the similarity measurement described in the preceding. The similarity measurement device can be engaged in data exchange with a data memory 2' in that the similarity conditions are stored.

Figure 3:
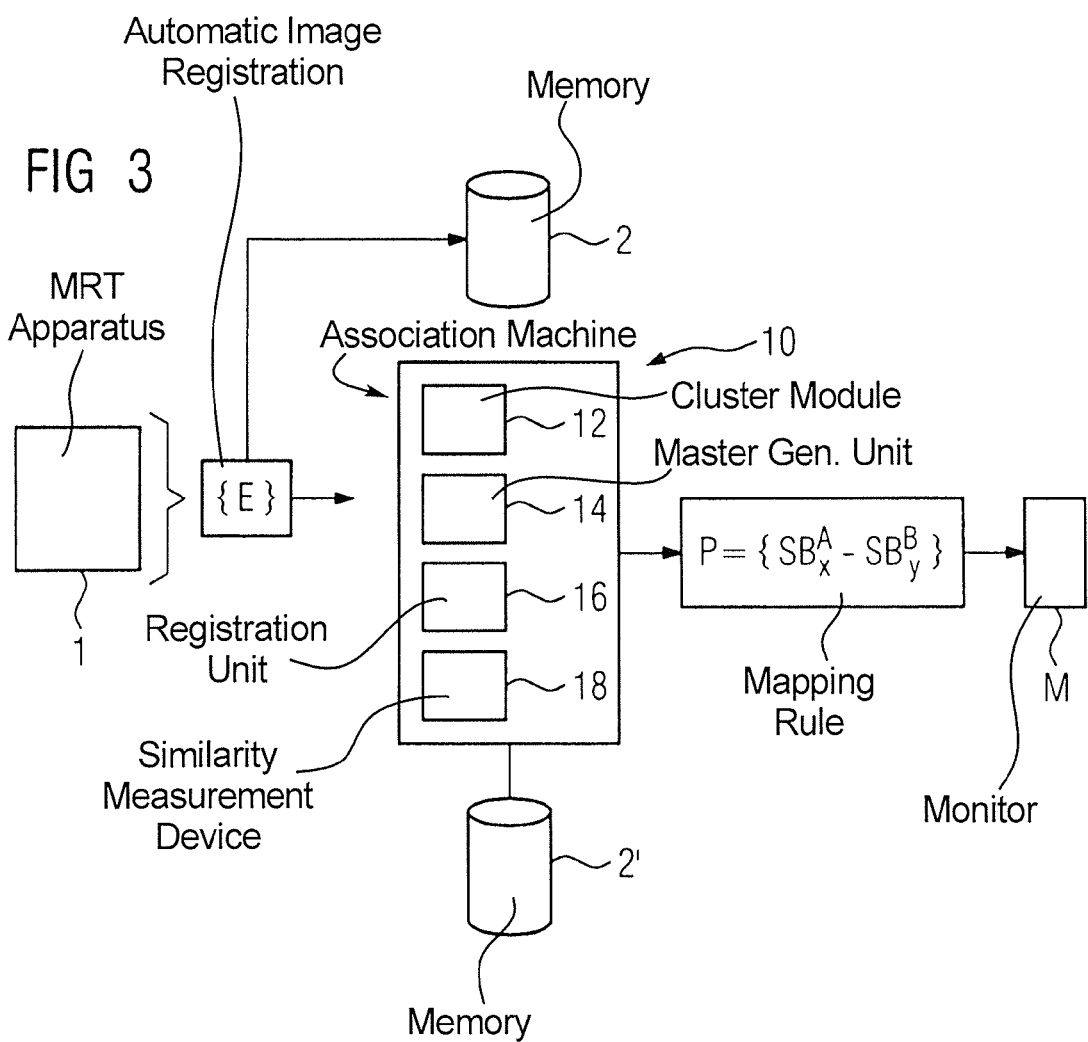
FIG. 3 is a schematic presentation of units of an association machine according to an embodiment of the invention.

The additional data memory is labeled with the reference character 2' in FIG. 3. All modules or units of the association machine 10 engage in data exchange with one another. The association machine 10 serves to transform the set with series E into a set of series pairs or series tuples P. This is identified in FIG. 3 in that a series pair to the right of the association machine 10—so to speak—is characterized as a series pair. The pair is represented by the reference character P. The pair P comprises an association of a series $SB_X$ of the current exam A with a series $SB_Y$ of the reference examination B. This is represented with the following mapping rule: $P=\{SB_X^A-SB_Y^A\}$. This association rule relates to the registration of a series pair. The association with multiple reference studies likewise lies within the scope of this invention. The series pairs that are generated in such a manner can then be presented synchronously on the at least one monitor M.

The preceding description related to the application of the method according to the invention to MRT imaging. However, it likewise lies within the scope of the invention to also apply the registration method according to the invention to other image modalities (for example CT, PET etc.). Furthermore, the application of the image registration is also not fixed to a specific form of acquisition. A study can thus in fact comprise multiple series; however, this is not absolutely necessary. The method according to the invention can be connected as an (external or integrated) software module within the scope of a finding process. Moreover, the method can be applied within the scope of the pre-processing. In principle, the invention is not limited to the application of a specific platform (operating system, computer network; cloud system, for example) or a specific underlying communication protocol (for example SOA, Service Oriented Architecture etc.), but rather can also be applied to variants.

Although modifications and changes may be suggested by those skilled in the art, it is the intention of the inventors to embody within the patent warranted hereon all changes and modifications as reasonably and properly come within the scope of their contributions to the art.

We claim as our invention:

1. A computerized device for automatic registration of image data of a medical image study, acquired with a medical imaging modality, and image data of at least one reference study, each of said medical image study and said at least one reference study comprising a plurality of series with each series comprising a plurality of image data sets, and each image data set having image position coordinates and a DICOM (Digital Imaging and Communications in Medicine) header associated therewith, and each of said series being stored in at least one data memory, said device comprising:

a cluster module configured to import image data of all series of at least said medical image study into said cluster module from said at least one data memory, and to automatically cluster said image data sets according to cluster criteria based exclusively on at least one of said image position coordinates and attributes of said DICOM header, thereby producing generated clusters, and to store said generated clusters;

a master generation unit configured to determine a master for all of the generated clusters;

a pair determination unit configured to automatically register the image data of said medical image study with said image data of said at least one reference study;

a registration unit configured to generate registered pairs among said data sets of said medical image study and said reference study by implementing a similarity measurement for each master from said medical image study by searching for at least one reference study that satisfies predetermined similarity conditions, or a search for a similar reference master of the reference study; and a monitor in communication with said registration unit, said registration unit being configured to cause said registered pairs to be displayed at said monitor.

2. A method for automatic registration of image data of a medical image study, acquired with a medical imaging modality, and image data of at least one reference study, each of said medical image study and said at least one reference study comprising a plurality of series with each series comprising a plurality of image data sets, and each image data set having image position coordinates and a DICOM (Digital Imaging and Communications in Medicine) header associated therewith, and each of said series being stored in at least one data memory, said method comprising:

in a cluster module of a processor, importing image data of all series of at least said medical image study into said cluster module from said at least one data memory, and automatically clustering said image data sets according to cluster criteria based exclusively on at least one of said image position coordinates and attributes of said DICOM header, thereby producing generated clusters, and to store said generated clusters;

in a master generation unit of said processor, determining a master cluster for all of the generated clusters;

in a pair determination unit of said processor, automatically registering the image data of said medical image study with said image data of said at least one reference study;

in a registration unit of said processor, generating registered pairs among said data sets of said medical image study and said reference study by implementing a similarity measurement for each master cluster from said medical image study by searching for at least one reference study that satisfies predetermined similarity conditions, or a search for a similar reference master cluster of the reference study; and at a monitor in communication with said registration unit, displaying said registered pairs.

3. A method as claimed in claim 2 comprising implementing a computerized consistency check of the registered pairs by calculating an average displacement vector for at least selected ones of the registered pairs, and designating registered pairs that deviate from said average displacement vector by more than a predetermined value as inconsistent.

4. A method as claimed in claim 3 comprising automatically implementing a computerized fallback strategy for each of said registered pairs that is identified as inconsistent, by automatically selecting a next-best candidate for a master of the reference study that best satisfies said similarity conditions, and iteratively repeating said consistency check and said fallback strategy.

5. A method as claimed in claim 2 comprising clustering said reference study according to the same cluster criteria used to cluster said medical image study, and also using said similarity measurement.

6. A method as claimed in claim 2 wherein said cluster criteria are based exclusively on said position coordinates.

7. A method as claimed in claim 2 wherein said similarity measurement comprises parsing DICOM header data in said DICOM header.

8. A method as claimed in claim 7 comprising parsing said DICOM header data by use of a name attribute that identifies an anatomical body region in the image data set associated with the respective DICOM header.

9. A method as claimed in claim 2 comprising implementing at least one of said clustering and said registering of said image data sets without access to any image data in said image data sets.

10. A method as claimed in claim 2 comprising clustering said image data sets by implementing an optimization in which each of said series is analyzed as to a distance from the cluster master associated therewith and adjacent cluster masters and, if the respective cluster is a shorter distance to one of the adjacent cluster masters, shifting the image series of the respective cluster into the adjacent cluster master having said shorter distance.

11. A method as claimed in claim 2 comprising determining said master by defining a series as said master that has a largest area coverage and a highest resolution.

12. A non-transitory, computer-readable data storage medium encoded with programming instructions, said data storage medium being loaded into a computerized device having access to at least one data memory in which image data sets of a medical image data study and image data sets of at least one reference study are stored, each of said medical image study and said at least one reference study comprising a plurality of series and each of said series comprising a plurality of image data sets, and each of said image data sets having image position coordinates and a DICOM (Digital Imaging and Communications in Medicine) header associated therewith, said programming instructions causing said computerized device to:

in a cluster module, import image data of all series of at least said medical image study into said cluster module from said at least one data memory, and automatically cluster said image data sets according to cluster criteria based exclusively on at least one of said image position coordinates and attributes of said DICOM header, thereby producing generated clusters, and store said generated clusters;

in a master generation unit, determine a master for all of the generated clusters;

in a pair determination unit, automatically register the image data of said medical image study with said image data of said at least one reference study;

in a registration unit, generate registered pairs among said data sets of said medical image study and said reference study by implementing a similarity measurement for each master from said medical image study by searching for at least one reference study that satisfies predetermined similarity conditions, or a search for a similar reference master of the reference study; and cause said registered pairs to be displayed at a monitor in communication with said registration unit.

\* \* \* \* \*